United States Patent
Ronda et al.

(10) Patent No.: US 9,315,726 B2
(45) Date of Patent: Apr. 19, 2016

(54) MIXED OXIDE MATERIALS

(71) Applicant: KONINKLIJKE PHILIPS N.V., Eindhoven (NL)

(72) Inventors: Cornelis Reinder Ronda, Aachen (DE); Jacobus Gerardus Boerekamp, Someren (NL); Daniela Buettner, Aachen (DE); Anne-Marie Andree Van Dongen, Waalre (NL); Herfried Karl Wieczorek, Aachen (DE); Sandra Johanna Maria Paula Spoor, Eindhoven (NL); Silvan Djohan, Rijswijk (NL); Wilhelmus Cornelis Keur, Weert (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/773,413

(22) PCT Filed: Mar. 21, 2014

(86) PCT No.: PCT/IB2014/060019
§ 371 (c)(1),
(2) Date: Sep. 8, 2015

(87) PCT Pub. No.: WO2014/155256
PCT Pub. Date: Oct. 2, 2014

(65) Prior Publication Data
US 2016/0024380 A1    Jan. 28, 2016

Related U.S. Application Data

(60) Provisional application No. 61/805,261, filed on Mar. 26, 2013.

(51) Int. Cl.
| | | |
|---|---|---|
| G01T 1/20 | (2006.01) | |
| C09K 11/77 | (2006.01) | |
| G01T 1/202 | (2006.01) | |
| A61B 6/03 | (2006.01) | |
| A61B 6/00 | (2006.01) | |

(52) U.S. Cl.
CPC ........... *C09K 11/7774* (2013.01); *A61B 6/03* (2013.01); *A61B 6/4208* (2013.01); *G01T 1/2023* (2013.01)

(58) Field of Classification Search
CPC .... C09K 11/7744; A61B 6/03; A61B 6/4208; G01T 1/2023
See application file for complete search history.

(56) References Cited

U.S. PATENT DOCUMENTS

| | | |
|---|---|---|
| 5,938,974 A | 8/1999 | Marking et al. |
| 6,168,731 B1 | 1/2001 | Hampden-Smith et al. |
| 6,630,077 B2 | 10/2003 | Shiang et al. |
| 7,076,020 B2 * | 7/2006 | Kanai et al. .................... 378/19 |
| 7,252,789 B2 | 8/2007 | Venkataramani et al. |

(Continued)

FOREIGN PATENT DOCUMENTS

| | | |
|---|---|---|
| EP | 1043383 A1 | 10/2000 |
| JP | 2012158485 A | 8/2012 |

(Continued)

*Primary Examiner* — Marcus Taningco

(57) ABSTRACT

The present invention relates to mixed oxide materials, methods for their preparation, detectors for ionizing radiation and CT scanners. In particular, a mixed oxide material is proposed having the formula $(Y_w Tb_x)_3 Al_{5-y} Ga_y O_{12}{:}Ce_z$, wherein $0.01 \leq w \leq 0.99$, $0.01 \leq x \leq 0.99$, $0 \leq y \leq 3.5$ and $0.001 \leq z \leq 0.10$ and wherein $w+x+3{*}z=1$, whereby the mixed oxide material is doped with at least 10 ppm V.

12 Claims, 2 Drawing Sheets

(56) References Cited

U.S. PATENT DOCUMENTS

| | | |
|---|---|---|
| 8,057,702 B2 | 11/2011 | Ronda et al. |
| 2004/0084655 A1 | 5/2004 | Vartuli et al. |
| 2008/0047482 A1* | 2/2008 | Venkataramani ................ 117/7 |
| 2008/0246004 A1* | 10/2008 | Krishna et al. ......... 252/301.4 R |

FOREIGN PATENT DOCUMENTS

| | | |
|---|---|---|
| JP | 2012184397 A | 9/2012 |
| WO | 2008012712 A1 | 1/2008 |
| WO | 2012066425 A2 | 5/2012 |
| WO | 2013015454 A2 | 1/2013 |

* cited by examiner

MIXED OXIDE MATERIALS

CROSS REFERENCE TO RELATED APPLICATIONS

This application is a national filing of PCT application Serial No. PCT/IB2014/060019, filed Mar. 21, 2014, published as WO 2014/155256 A1 on Oct. 2, 2014, which claims the benefit of U.S. provisional application Ser. No. 61/805,261 filed Mar. 26, 2013, which is incorporated herein by reference.

FIELD OF THE INVENTION

The present invention relates to mixed oxide materials, methods for their preparation, detectors for ionizing radiation and CT (Computed Tomography) scanners.

BACKGROUND OF THE INVENTION

Detectors for ionizing radiation and, in particular, solid state detectors for ionizing radiation are, e.g., widely used in CT scanners. Such solid state detectors for ionizing radiation comprise, broadly speaking, two main subunits. The first subunit comprises a fluorescent component that is usually referred to as a scintillator or a phosphor which absorbs radiation and in response emits photons in the UV, the visible or the IR region. The second subunit comprises a photodetector which can detect the photons emitted by the scintillator or phosphor and produces corresponding electrical signals.

With regard to the above expressions "scintillator" and "phosphor", it needs to be noted that both are exchangeable terms and are to be understood within the scope of the invention to refer to solid state luminescent materials that, in response to a stimulation by ionizing radiation such as X-rays, $\beta$- or $\gamma$-radiation, emit radiation with photons of considerably lower energy.

The expression "ionizing radiation" within the scope of the invention refers to electromagnetic radiation having energy higher than that of ultraviolet radiation.

Detectors for ionizing radiation find broad application in X-ray-based detecting and imaging systems. One of the major medical applications for such detectors and scintillators is in CT scanners.

In particular for their application in CT scanners, it is preferable if those scintillators show a high light yield, so that the CT scanner can be run with as low a radiation dose for the patient as possible. Furthermore, the scintillators used in modern CT scanners should have as low an afterglow as possible, as otherwise the scanning process must be slowed down (e.g. by reducing the rotation frequency) to reduce the influence of the afterglow in subsequent images, affecting the speed of the examination.

Finally, it is also desirable that the scintillators are as transparent as possible to visible light, as otherwise scattering of the photons produced by the interaction between the ionizing radiation and the scintillator occurs, which results in effective background noise during the imaging process, due to optical absorption of the scintillation light in the scintillator.

The two materials that are at the moment commonly used as scintillators for CT scanners are scintillator materials based on $Gd_2O_2S$ doped with Pr (GOS) and $(Y, Gd)_2O_3$ doped with Eu. While those two materials already give reasonable results, it has been shown that GOS, due to the fact that it is not transparent to visible light but merely translucent, shows a reasonably high scattering leading to undesirable effective noise, whereas the $(Y, Gd)_2O_3$:Eu based systems show a notable afterglow which could be improved upon for the next generation of CT scanners by replacing this scintillator.

SUMMARY OF THE INVENTION

It is an object of the present invention to provide a mixed oxide material, a method for its preparation, a scintillator, a detector for ionizing radiation and a CT scanner, wherein the scintillator shows a high light yield, a very low afterglow and a high transparency.

In a first aspect of the present invention, a mixed oxide material having the formula $(Y_w Tb_x)_3 Al_{5-y} Ga_y O_{12}:Ce_z$ is presented, wherein $0.01 \leq w \leq 0.99$, $0.01 \leq x \leq 0.99$, $0 \leq y \leq 3.5$ and $0.001 \leq z \leq 0.10$ and wherein $w+x+3*z=1$, whereby the mixed oxide material is doped with at least 10 ppm V, preferably at least 25 ppm V.

In a further aspect of the present invention, a method for preparing a mixed oxide material as described above is presented that comprises the following steps: a) providing $Y_2O_3$, $CeO_2$, $Tb_4O_7$, $Al_2O_3$ and $Ga_2O_3$ in proportions suitable to obtain the desired mixed oxide, b) impregnating one or several of the solids of step a) with a source of V in the desired amount, c) combining and milling the solids of step a) and step b) in the presence of a suitable dispersant, to obtain a slurry, d) drying the slurry of step c) to obtain a mixed powder, and e) sintering the mixed powder of step d) at a temperature of at least 1400° C. for at least 1 h.

In a further aspect of the present invention, a scintillator is presented that comprises the above-mentioned mixed oxide material.

In a further aspect of the present invention, a detector for ionizing radiation is presented that comprises the above mentioned mixed oxide material or the above-mentioned scintillator in combination with at least one photodetector.

In a further aspect of the present invention, a CT scanner is presented that comprises at least one detector as described above.

$(Y_w Tb_x)_3 Al_{5-y} Ga_y O_{12}:Ce_z$ based materials have been known for some time to be able to interact with ionizing radiation and, as a result, release photons, i.e. to have scintillator properties. The materials known so far, though, show an afterglow that is so high that they have been considered not suitable for modern CT scanners. It has now been found that by doping the above-mentioned mixed oxide materials with minute quantities of vanadium, the afterglow can be reduced significantly without sacrificing the light yields too strongly and therefore creating a scintillator material that is suitable for application in modern CT scanners.

In an embodiment, the mixed oxide material is doped with 10 to 250 ppm V, preferably 25 to 200 ppm V.

It has been shown that the addition of vanadium to the mixed oxide material in the above-mentioned quantity ranges leads to a good balance between improvements of the afterglow without significant losses in the light yield.

In another embodiment of the mixed oxide material, $0.1 \leq w \leq 0.9$, preferably $0.2 \leq w \leq 0.8$, more preferably $0.3 \leq w \leq 0.6$ and even more preferably $0.35 \leq w \leq 0.5$.

In another embodiment of the mixed oxide material, $0.1 \leq x \leq 0.9$, preferably $0.2 \leq x \leq 0.8$, more preferably $0.4 \leq x \leq 0.7$ and even more preferably $0.5 \leq x \leq 0.65$.

In another embodiment of the mixed oxide material, $1 \leq y \leq 3.5$ preferably $2 \leq y \leq 3.5$ and more preferably $2.5 \leq y \leq 3.5$.

In still another embodiment of the mixed oxide material, $0.005 \leq z \leq 0.05$, preferably $0.005 \leq z \leq 0.02$ and more preferably $z=0.01$.

In a further embodiment, the mixed oxide material has the formula $(Y_{0.395}Tb_{0.595})_3Al_5O_{12}:Ce_{0.01}$ and is doped with at least 10 ppm V, preferably 10 to 250 ppm V, and, in particular, 25 to 200 ppm V.

It has been shown that mixed oxide materials in the above-mentioned composition ranges lead to particularly effective scintillator materials having a high light yield and a low afterglow.

In a further embodiment, the mixed oxide material is a single crystalline or a polycrystalline material.

In an embodiment of the above-mentioned method, a flux material is added in step c) when combining the solids of step a) step b).

By adding a flux material in step c), the diffusion of the different ions during the sintering of step d) can be improved, leading to higher quality material at lower sintering temperatures.

In a further embodiment, the detector further comprises a second mixed oxide material or scintillator, whereby the second mixed oxide material or second scintillator has a higher density than the above-described mixed oxide material or scintillator.

Through a combination of two different scintillator materials having a different density, X-rays of different energy levels can be detected, whereby the material of lower density generally detects X-rays of a lower energy, and the material of higher density generally detects X-rays of a higher energy. By creating detectors which comprise two different scintillators or scintillator materials, a detector can be created that detects two different types of X-rays which, for example, in CT scanners gives more information about the body or part of the body that is being examined.

DETAILED DESCRIPTION OF THE INVENTION

Examples

Examples 1 to 4

Stoichiometric amounts of $Y_2O_3$ (Rhodia), $CeO_2$ (Neo Materials), $Tb_4O_7$ (Guangdong and Neo Materials), $Al_2O_3$ (Baikowski) were weighed in, in proportions to create mixed oxide materials having the formula $(Y_{0.395}Tb_{0.595})_3Al_5O_{12}:Ce_{0.01}$. In order to dope these materials with 25 ppm, 50 ppm, 100 ppm and 200 ppm, respectively of V, a corresponding amount of $NH_4VO_3$ was dissolved in ethanol, mixed with the $Al_2O_3$, precipitated and dried on a rotary evaporator. The modified $Al_2O_3$ obtained this way was then employed in the solid state synthesis of the desired mixed oxides. The solid starting materials were mixed and milled with heptane in agate pots. After the mixing process, the samples were dried in a tube oven to remove the mixing liquid, and the samples were sintered in a horizontal tube furnace (Entech 01820 series) at 1550° C. in an aluminium crucible for 4 hours in a $H_2/N_2$ flow in order to reduce $Ce^{4+}$ to $Ce^{3+}$ and $Tb^{4+}$ to $Tb^{3+}$.

The obtained samples were tested for photoluminescence, whereby the photoluminescence emission spectra were recorded at room temperature using a xenon lamp with an Edinburgh instruments FLSP920 spectrometer featuring double monochromators to improve resolution and to reduce stray light. Afterglow measurements were performed using X-ray excitation and a photodiode. The light yield was measured by determining the area under the emission curve and expressed as a percentage yield compared to Comparative Example 1 in each of the tables.

The results of the measurements compared to $(Y_{0.395}Tb_{0.595})_3Al_5O_{12}:Ce_{0.01}$ without vanadium are shown below in Tables 1 and 2.

Table 1, light yields for Examples 1 to 4 compared to $(Y_{0.395}Tb_{0.595})_3Al_5O_{12}:Ce_{0.01}$ without the addition of vanadium. Percentage values are relative to Comparative Example 1.

|  |  | 280 nm $Tb^{3+}$ band excitation | | 345 nm $Ce^{3+}$ band excitation | | 378.5 nm $Tb^{3+}$ $^7F_6$-$^5D_3$ excitation | |
|---|---|---|---|---|---|---|---|
|  | V Content | Area | % Light Yield | Area | % Light Yield | Area | % Light Yield |
| Comparative Example 1 | 0 ppm | 2.26E+08 | 100.0 | 8.33E+07 | 100.0 | 7.28E+07 | 100.0 |
| Example 1 | 25 ppm | 2.14E+08 | 94.9 | 8.75E+07 | 105.0 | 8.24E+07 | 113.2 |
| Example 2 | 50 ppm | 1.97E+08 | 87.1 | 7.95E+07 | 95.4 | 7.37E+07 | 101.2 |
| Example 3 | 100 ppm | 1.87E+08 | 82.6 | 7.41E+07 | 88.9 | 6.43E+07 | 88.3 |
| Example 4 | 200 ppm | 1.59E+08 | 70.5 | 7.02E+07 | 84.3 | 5.99E+07 | 82.3 |

BRIEF DESCRIPTION OF THE DRAWINGS

These and other aspects of the invention will be apparent from and elucidated with reference to the embodiments and examples described hereinafter. In the following drawings

Figure 1:
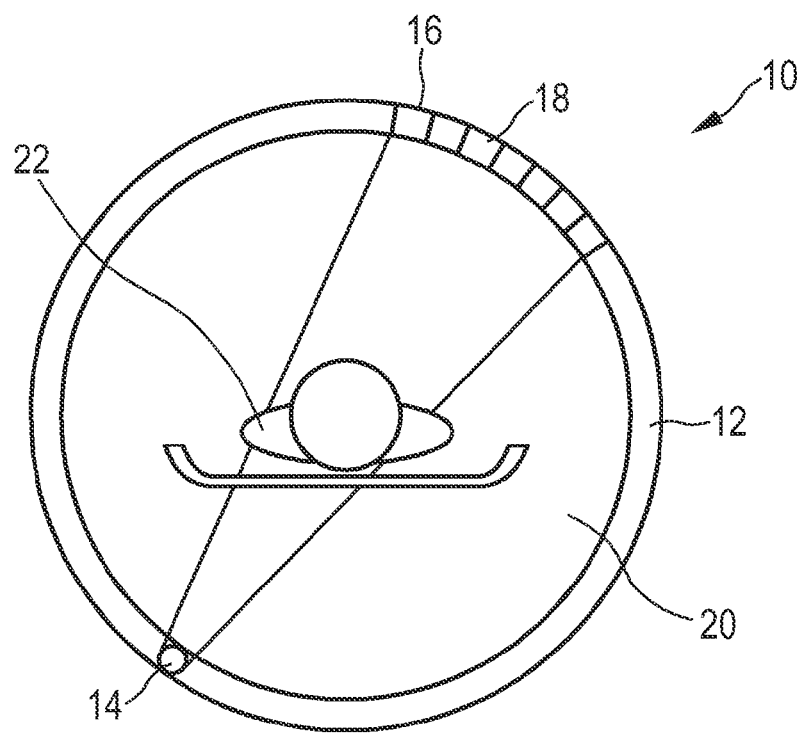
FIG. 1 shows a schematic diagram of a CT scanner according to the present invention.

Table 2, afterglow for Examples 1 to 4 compared to $(Y_{0.395}Tb_{0.595})_3Al_5O_{12}:Ce_{0.01}$ without the addition of vanadium. Percentage values are relative to Comparative Example 1. Ppm values are relative to initial intensity of the corresponding material.

|  | % afterglow after 5 ms (relative to Comparative Example 1) | | PD 5 ms [ppm] | | PD 500 ms [ppm] | | PD 2100 ms [ppm] | |
|---|---|---|---|---|---|---|---|---|
|  |  |  | μ | σ | μ | σ | μ | σ |
| Comparative Example 1 | 100.0 | | 4628 | 15 | 122 | 1 | 43 | 1 |

-continued

| | % afterglow after 5 ms (relative to Comparative Example 1) | PD 5 ms [ppm] | | PD 500 ms [ppm] | | PD 2100 ms [ppm] | |
|---|---|---|---|---|---|---|---|
| | | μ | σ | μ | σ | μ | σ |
| Example 1 | 5.7 | 263 | 9 | <10 | | <10 | |
| Example 2 | 8.2 | 380 | 65 | 31 | 1 | <10 | |
| Example 3 | 10.3 | 476 | 42 | 10 | 2 | 12 | 3 |
| Example 4 | 2.3 | 108 | 7 | <10 | | <10 | |

Comparative Examples 1 to 4

As comparative examples, $(Y_{0.0395}Tb_{0.595})_3Al_5O_{12}:Ce_{0.01}$ doped with Ti, Cr and Mn as well as $(Y_{0.395}Tb_{0.595})_3Al_5O_{12}:Ce_{0.01}$ without the addition of any dopant was prepared.

The synthesis of the Comparative Examples took place in analogy to the synthesis of Examples 1 to 4 with the $NH_4VO_3$ being omitted or replaced with Ti-n-butoxide, Cr$(NO_3)_3 \cdot 9H_2O$, and $Mn(NO_3)_2 \cdot 4H_2O$ respectively. A dopant level of 50 ppm was used for all Comparative Examples comprising a dopant.

The analysis of the materials obtained according to Comparative Examples 1 to 4 took place according to the conditions described above for Examples 1 to 4 and the results are shown below in Tables 3 and 4.

Table 3, light yields for Comparative Examples 1 to 4. Percentage values are relative to Comparative Example 1.

| | 280 nm Tb3+ band excitation | | |
|---|---|---|---|
| | Dopant | Area | % Light Yield |
| Comparative Example 1 | none | 6429590 | 100.0 |
| Comparative Example 2 | Ti | 5734990 | 89.2 |
| Comparative Example 3 | Cr | 5907660 | 91.9 |
| Comparative Example 4 | Mn | 6055820 | 94.2 |

Table 4, afterglow for Comparative Examples 1 to 4. Percentage values are relative to Comparative Example 1. Ppm values are relative to initial intensity of the corresponding material.

| | % afterglow after 5 ms (relative to Comparative Example 1) | PD 5 ms [ppm] | | PD 500 ms [ppm] | | PD 2100 ms [ppm] | |
|---|---|---|---|---|---|---|---|
| | | μ | σ | μ | σ | μ | σ |
| Comparative Example 1 | 100.0 | 4628 | 15 | 122 | 1 | 43 | 1 |
| Comparative Example 2 | 49.4 | 2285 | 17 | 147 | 1 | 52 | 1 |
| Comparative Example 3 | 94.1 | 4355 | 40 | 115 | 1 | 39 | 1 |
| Comparative Example 4 | 268.1 | 12406 | 12 | 392 | 2 | 85 | 1 |

The data from the Examples and Comparative Examples show clearly that the addition of vanadium to the $(Y_{0.395}Tb_{0.595})_3Al_5O_{12}:Ce_{0.01}$ mixed oxide material significantly reduces the afterglow without impacting the light yield excessively. Furthermore, the Comparative Examples show that this seems to be a very specific effect for vanadium, as related d-group metals such as titanium, chrome or manganese do not show such an effect.

In FIG. 1, a CT scanner in its entirety is denoted with reference numeral 10. The CT scanner 10 comprises a rotating gantry 12 on which on opposing sides an X-ray source 14 and a detector array 16 are arranged. The detector array 16 consists of a number of individual X-ray detectors one of which is for exemplary purposes denoted here with the reference numeral 18. The rotating gantry 12 is arranged such that the X-ray source 14 and the detector array 16 are on opposing sides of an examination area 20 into which a patient 22 is inserted. In use, the X-ray source emits a wedge-shaped, cone-shaped or otherwise shaped X-ray beam directed into the examination area 20, in the instant case in the direction of a patient 22. The patient 22 can be linearly moved in a z direction (perpendicular to the plane of drawing), while the X-ray source 14 and, correspondingly, the detector array 16 rotate around the z axis. In general, the rotating gantry 12 rotates simultaneously with the linear advancement of the patient 22 leading to a generally helical trajectory of the X-ray source 14 and, correspondingly, the detector array 16 around the examination area 20. However, other imaging modes can also be employed, such as a single- or multi-slice imaging mode in which the gantry rotates as the subject support remains stationary, to produce a generally circular direction of the X-ray source 14 and, correspondingly, the detector array 16 over which an axial image is acquired.

As can be seen in the picture, the detector array 16 is arranged on the gantry 12 on the opposing side of the X-ray source 14, so that in use the X-rays emitted by the X-ray source 14 pass through e.g. a patient 22 and are then detected by the detector array 16. The detector array 16 generally comprises a multitude of detectors 18, whereby the detector array 16 can be a single line of detectors 18 or two-dimensional array of detectors 18. A more detailed explanation of the function of the detectors 18 within the detector arrays 16 is given below in respect to various embodiments of the detectors shown in FIGS. 2 to 4.

Figure 2:
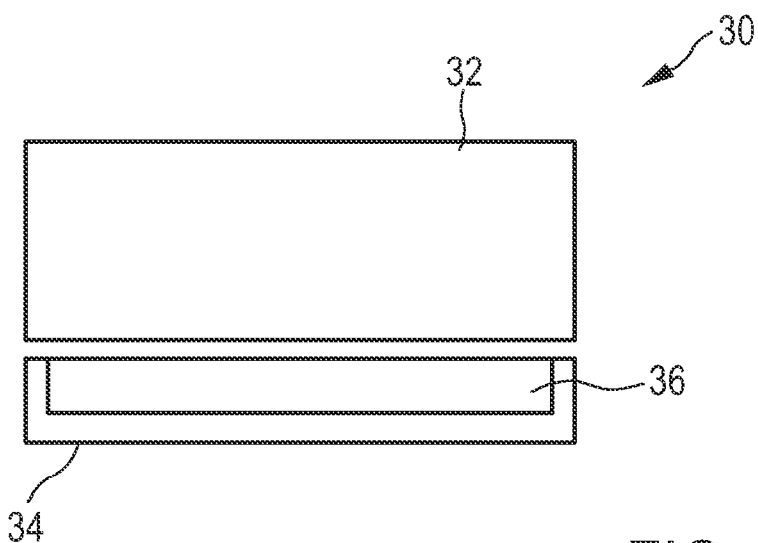
FIG. 2 shows a schematic diagram of a first embodiment of a detector for ionizing radiation according to the present invention.

In FIG. 2, a first embodiment of a detector for ionizing radiation is denoted in its entirety with reference numeral 30. The detector 30 comprises two subunits, namely the scintillator 32 and the photodetector 34. The photodetector 34 comprises a photodiode 36 which is arranged such that the active area of the photodiode 36 is facing the scintillator 32.

In use, the detector is arranged such that the scintillator 32 points towards the source of potential source of radiation to be detected. The scintillator 32 thereby e.g. consists of the material described above under Example 1. If ionizing radiation, for example X-rays, now impinges on the scintillator 32, the scintillator 32 interacts with those X-rays and, in response, releases one or multiple photons which are emitted from the scintillator 32 and can be detected by the photodiode 34 generating an electric signal indicating the presence of X-rays. In order to improve the yield of photons detected by the diode 34, the scintillator 32 can be covered on one or several sides not facing the photodetector with a material reflective to the emitted photons.

Figure 3:
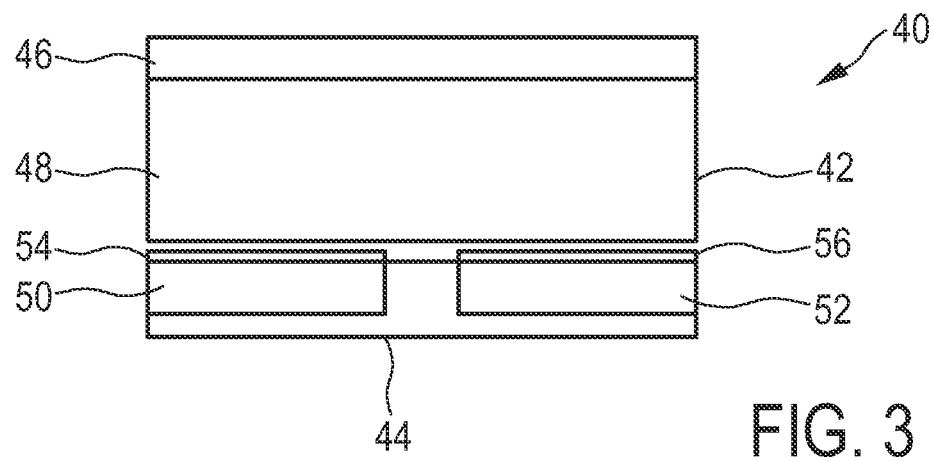
FIG. 3 shows a schematic diagram of a second embodiment of a detector for ionizing radiation according to the present invention.

In FIG. 3, a second embodiment of a detector for ionizing radiation is designated in its entirety with reference numeral 40. Again, this detector 40 comprises two subunits, namely a scintillator 42 and a photodetector 44. In contrast to the embodiment of FIG. 1, in this case the scintillator 42 consists of two different scintillator materials, a first scintillator material 46 and a second scintillator material 48. The first scintillator material 46, in the instant case, is the material of the above-mentioned Example 2, and the second scintillator material 48 is thereby a scintillator material having a higher density than the first scintillator material 46. In the instant case, the second scintillator material 48 is a $Gd_2O_2S$ doped with Pr.

Corresponding to the first scintillator material 46 and the second scintillator material 48, the photodetector 42 comprises two photodiodes, a first photodiode 50 and a second photodiode 52. In use, X-rays with different energies impinge on the detector 40 from top, i.e. from the direction of the first scintillator material 46. Due to its lower density, the first scintillator material 46 absorbs X-rays of lower energy and in response thereto emits photons of a first frequency. After passing through the first scintillator material 46, the X-rays strike the second scintillator material 48, whereby through the interaction with the second scintillator material 48, photons of a second wavelength are emitted.

The first photodiode 50 is now equipped with a first filter 54 which filters out photons of the second wavelength, ensuring that only the photons of the first wavelength, i.e. the photons generated by the first scintillator material 46, are detected by the first photodiode 50.

Correspondingly, the second photodiode 52 is equipped with a second filter 56 which blocks photons of the first wavelength, ensuring that only photons of the second wavelength, i.e. photons generated by the second scintillator material 48, reach the second photodiode 52 and are detected thereby.

Through the above-mentioned set-up, it is possible with the detector 40 to detect and differentiate X-rays of two different energy levels and create corresponding signals increasing the amount of information available in the CT scan.

Figure 4:
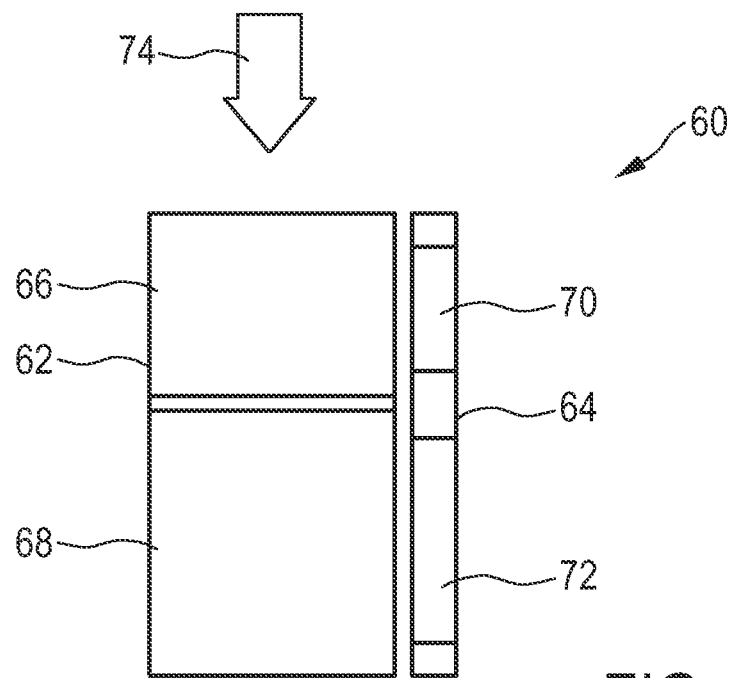
FIG. 4 shows a schematic diagram of a third embodiment of a detector for ionizing radiation according to the present invention.

In FIG. 4, a third embodiment of a detector for ionizing radiation is designated in its entirety with reference numeral 60. The detector for ionizing radiation 60 is similar in function to the detector 40 of FIG. 3, but shows a different design.

Again, the detector 60 consists of a scintillator 62 and a photodetector 64. In this case again the scintillator 62 consists of a first scintillator material 66 and a second scintillator material 68. The first scintillator material 66 is, thereby, for example the material of Example 3, whereby the second scintillator material 68 again is Pr doped $Gd_2O_2S$, i.e. a material of higher density than the first scintillator material 66. In contrast to the embodiment of FIG. 3, in FIG. 4 the photodetector 64 is not arranged underneath the scintillator 62 but on the side of it, whereby a first photodiode 70 is arranged on the side of the first scintillator material 66 and a second photodiode 72 is arranged on the side of the second scintillator material 68, when seen in the direction of the incoming ionizing radiation to be detected, as indicated by arrow 74.

Both scintillator materials 66 and 68 are covered on those sides which do not face the first photodiode 70 and second photodiode 72, respectively, with a coating that is reflective to photons in the wavelength range emitted by the first and second scintillator material 66 and 68, respectively, yet transparent to ionizing radiation.

In use, the ionizing radiation travels in the direction indicated by arrow 74 towards the first scintillator material 66, whereby, due to the lower density, the lower energy part of the ionizing radiation interacts with the first scintillator material 66 and stimulates the emission of one or several photons. Due to the reflective coating, on the outside of the first scintillator material 66, the photons can only exit the first scintillator material 66 towards the first photodiode 70 and are detected thereby. After traveling through the first scintillator material 66, the ionizing radiation travels to the second scintillator material 68, whereby, due to the fact that the density of the second scintillator material 68 is higher than the first scintillator material 66, higher energy radiation is absorbed and, as a result, a second set of photons is generated. Again, due to the fact that the second scintillator 68 material is covered by reflective material on those sides not facing the second photodiode, the photons can only exit the second scintillator material 68 towards the second photodiode 72 and are detected thereby.

Again, due to the fact that each scintillator material interacts with radiation of a specific energy level and in response emits photons which are directed to specific photodiodes and detected thereby, different X-rays can be detected with the detector for ionizing radiation creating more information, for example about a body to be investigated in a CT scanner.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A mixed oxide material having the formula $(Y_wTb_x)_3Al_{5-y}Ga_yO_{12}:Ce_z$, wherein $0.01 \leq w \leq 0.99$, $0.01 \leq x \leq 0.99$, $0 \leq y \leq 3.5$ and $0.001 \leq z \leq 0.10$ and wherein $w+x+3*z=1$; whereby the mixed oxide material is doped with at least 10 ppm V.

2. The mixed oxide material according to claim 1, whereby the material is doped with 10 to 250 ppm V.

3. The mixed oxide material according to claim 1, whereby $0.1 \leq w \leq 0.9$.

4. The mixed oxide material according to claim 1, whereby $0.1 \leq x \leq 0.9$.

5. The mixed oxide material according to claim 1, whereby $1 \leq y \leq 3.5$.

6. The mixed oxide material according to claim 1, whereby $0.005 \leq z \leq 0.05$.

7. The mixed oxide material according to claim 1, whereby the material is a single-crystalline or polycrystalline material.

8. A method for producing a mixed oxide material according to claim 1, comprising the following steps;
   a) providing $Y_2O_3$, $CeO_2$, $Tb_4O_7$, $Al_2O_3$ and $Ga_2O_3$ in proportions suitable to obtain the desired mixed oxide,
   b) impregnating one or several of the solids of step a) with a source of V in the desired amount,
   c) combining and milling the solids of step a) and step b) in the presence of a suitable dispersant, to obtain a slurry,
   d) drying the slurry of step c) to obtain a mixed powder, and
   e) sintering the mixed powder of step d) at a temperature of at least 1400° C. for at least 1 h.

9. The method according to claim 8, whereby in step c) a flux material is added when combining the solids of step a) and step b).

10. A scintillator comprising a mixed oxide material according to claim 1.

11. A detector for ionizing radiation comprising a mixed oxide material according to claim 1 or a scintillator in combination with at least one photodetector.

12. A CT scanner comprising at least one detector according to claim 11.

* * * * *